United States Patent [19]
Clement et al.

[11] Patent Number: 5,350,384
[45] Date of Patent: Sep. 27, 1994

[54] CATHETER GUIDE AND CLAMP INSTRUMENT

[75] Inventors: Gordon S. Clement, Norristown; Christopher Kebert, Philadelphia, both of Pa.

[73] Assignee: Pilling Co., Ft. Washington, Pa.

[21] Appl. No.: 993,521

[22] Filed: Dec. 18, 1992

Related U.S. Application Data

[63] Continuation of Ser. No. 683,270, Apr. 10, 1991, abandoned.

[51] Int. Cl.$^5$ ............................................. A61F 11/00
[52] U.S. Cl. .................................. 606/108; 606/206; 604/158
[58] Field of Search ........................................ 128/4–6; 606/108, 205–211, 51, 52; 604/158, 159, 164, 264, 280

[56] References Cited

U.S. PATENT DOCUMENTS

| | | | |
|---|---|---|---|
| 4,578,058 | 3/1986 | Grandon | 604/93 |
| 4,700,694 | 10/1987 | Shishido | 128/6 |
| 4,905,669 | 3/1990 | Bullard et al. | 128/6 |
| 5,009,643 | 4/1991 | Reich et al. | 606/185 |
| 5,040,548 | 8/1991 | Yock | 604/96 |
| 5,044,369 | 9/1991 | Sahota | 604/96 |
| 5,129,889 | 7/1992 | Hahn et al. | 604/158 |
| 5,131,379 | 7/1992 | Sewell, Jr. | 606/159 |

OTHER PUBLICATIONS

Karl Storz brochure *Minimally Invasive Laparoscopic Procedures*, four (4) pages, identification mark on last pp. C430-5000-890, (publication date unknown).
Cabot Instruments document, no title, one (1) page, with Order No. 004547-902 for Cholangiogram Instrument. (publication date unknown).
Solos Endoscopy brochure entitled *Solos Endoscopy-Laparoscopic Cholecystectomy-Complete Instrumentation and Equipment*, one (1) page with GS-7100 for Cholangiogram Clamp and GS-7150 for Cook Cholangiogram Guide, copyrighted 1990. (publication date unknown).
Karl Storz document entitled *Laporoscopic Cholecystectomy*, one (1) page, identification mark LCC 7. (publication date unknown).
Surgimedics advertisement entitled *600,000 Good Reasons to Use Our Laporoscopic Cholangiography Catheter*, one (1) page, copyrighted 1991 (publication date unknown).

*Primary Examiner*—John D. Yasko
*Assistant Examiner*—Ronald K. Stright, Jr.
*Attorney, Agent, or Firm*—Howson and Howson

[57] ABSTRACT

A surgical instrument for use in operative cholangiography associated with a laparoscopic cholecystectomy. A catheter guide and clamp are combined in a single instrument manipulatable through a conventional trocar. The guide includes a straight elongate tube with an oblique exit opening for introducing a catheter tip through an incision in the cystic duct and laterally deflecting the inserted tip toward the common duct. The clamp longitudinally movable, and is operated from the proximal end of an actuator tube and stem to seal the duct around the catheter to prevent any fluid injected into the duct from leaking out through the incision.

13 Claims, 3 Drawing Sheets

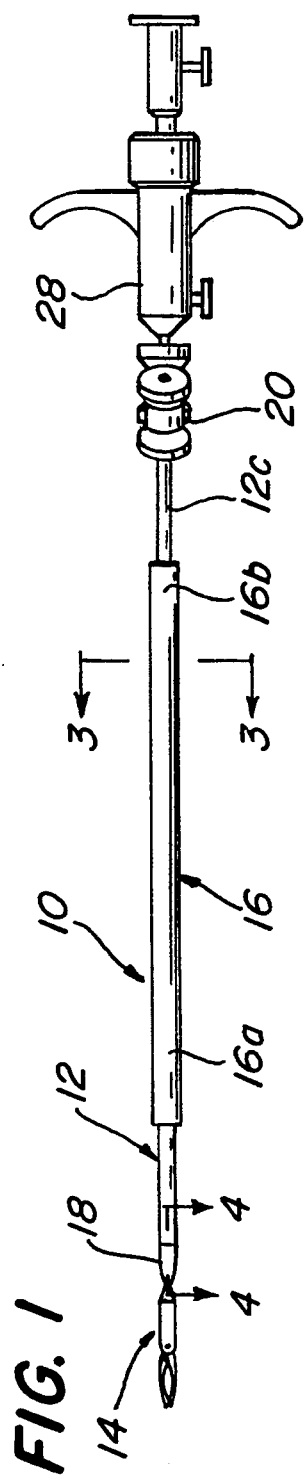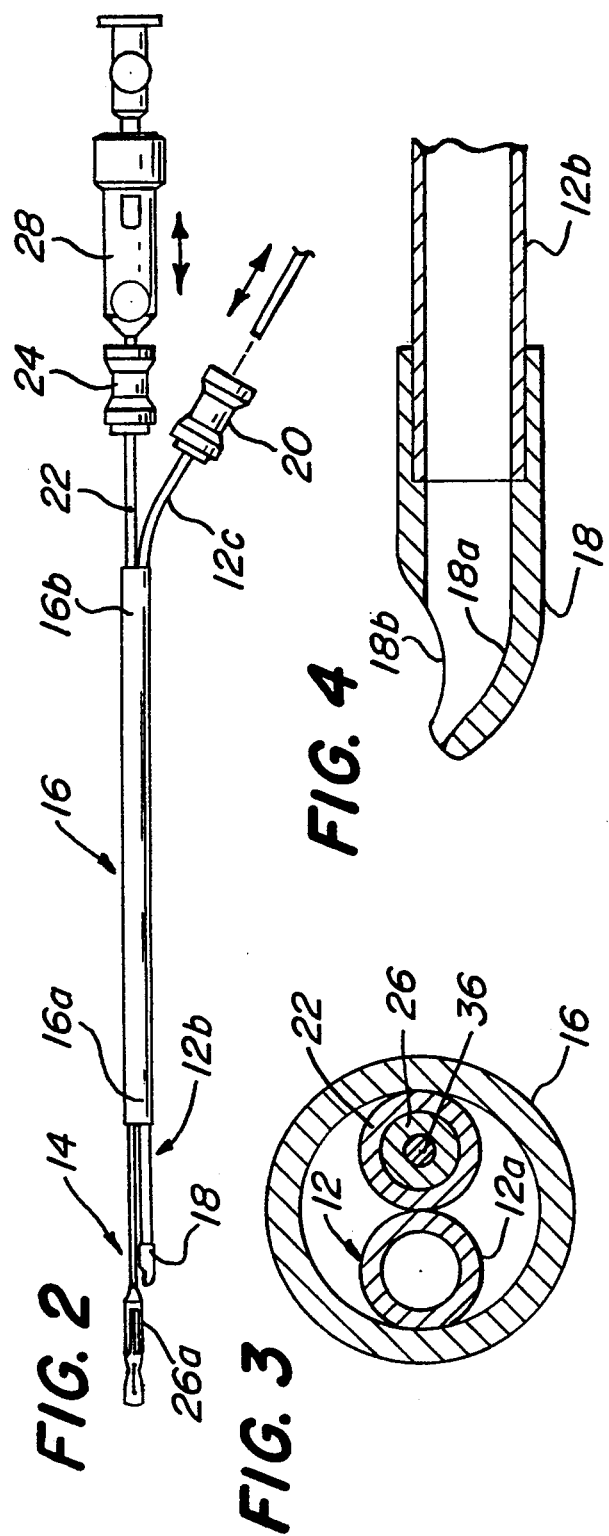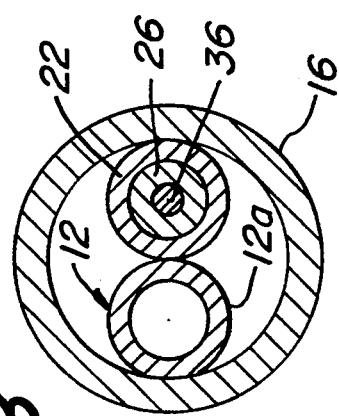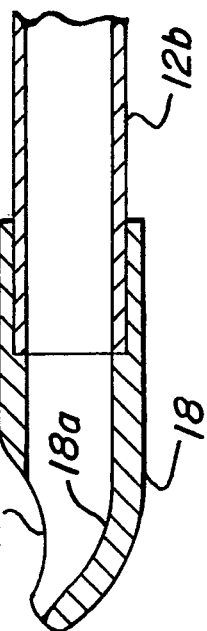

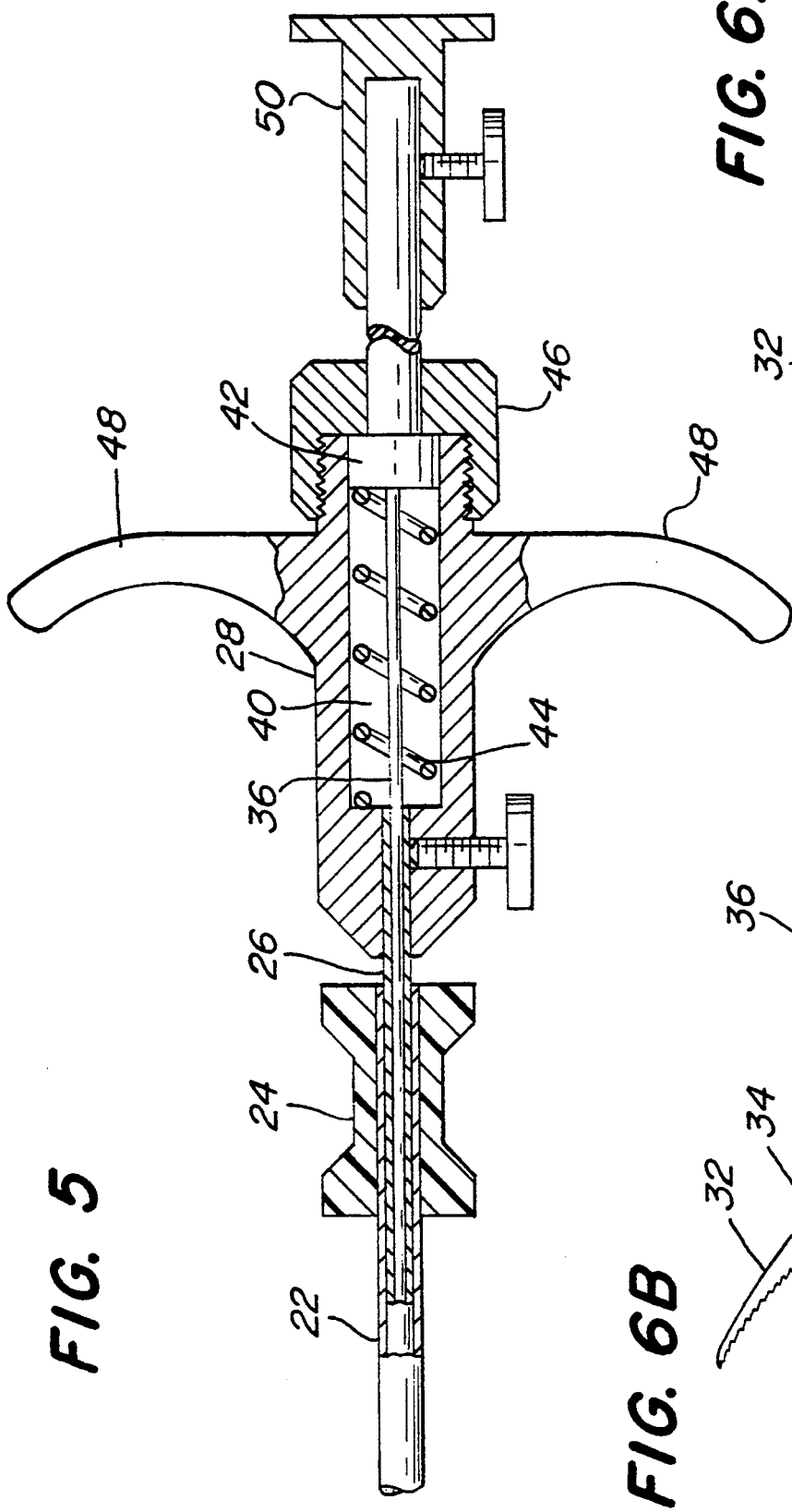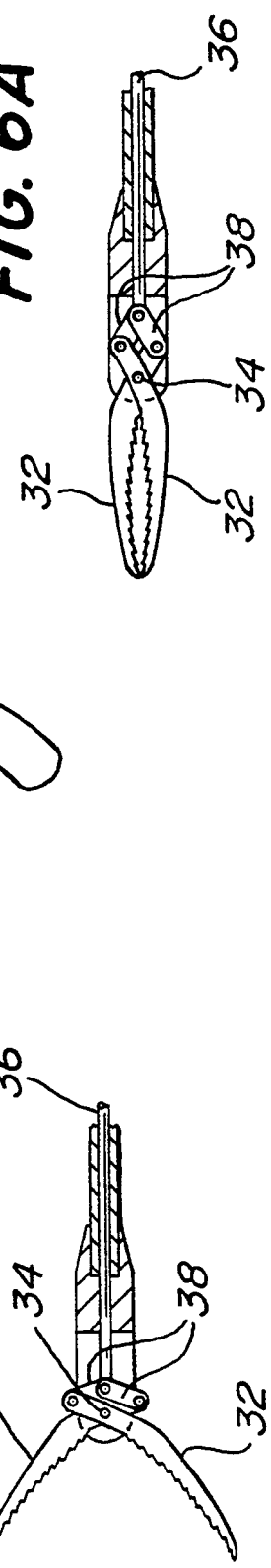

CATHETER GUIDE AND CLAMP INSTRUMENT

This is a continuation of application Ser. No. 07/683,270, filed on Apr. 10, 1991 now abandoned.

BRIEF SUMMARY OF THE INVENTION

This invention relates generally to instruments for performing percutaneous surgical procedures, and more particularly to a catheter guide and clamp instrument for use in surgical procedures such as operative cholangiography.

A relatively new surgical procedure which significantly streamlines the recovery process of patients who undergo gallbladder removal is the laparoscopic cholecystectomy. It is carried out by the use of fiberoptics, video and a flexible endoscope to view and gain access to a diseased gallbladder without a major incision. Several pinhole incisions are made in the abdomen to allow careful insertion of various instruments. One incision made in the umbilicus receives a viewing endoscope which conducts an image of internal organs in the abdominal cavity through an optical fiber bundle to a small video camera. The image as seen by the camera is displayed on two television monitors located on opposite sides of the operating table for observation by the members of the surgical team. Additional incisions are made on the patient's right side just under the costal margin or rib cage for insertion of other instruments and for coordination of each delicate maneuver. Nitrous oxide, carbon dioxide, or air is injected through one of these instruments, expanding the abdominal cavity to allow the surgeons more maneuverability in the operating region. Still another small incision is made between the umbilicus and the xiphoid of the sternum for a surgeon to insert a trocar and dissect a course toward the cystic duct by separating and spreading tissues using scissors, forceps, and sometimes a laser. At the same time, instruments inserted through several of the other incisions adjacent to the costal margin lift the liver to expose the cystic duct and gallbladder. The gallbladder is then clamped off, drained of fluid and pulled out through a trocar in one of the incisions.

In this procedure it is important to determine whether or not any gall stones are present in the cystic duct and the common duct. These stones must be dislodged or removed. An operative cholangiography is therefore performed. Cholangiography entails the injection of a radiopaque dye or contrast medium through a small incision in the cystic duct near the gallbladder and taking X rays. The incision is made by scissors or a scalpel passed through a trocar extending through one of the incisions adjacent to the costal margin. With the trocar still in place, the cutting instrument is withdrawn. A catheter is then inserted through the trocar into the incision and manipulated so that its exit opening extends toward the common duct, rather than toward the gallbladder. The cystic duct is clamped around the extended tip of the catheter to prevent the dye subsequently introduced from escaping into the abdominal cavity and obscuring visibility of the biliary duct region both for X-rays and for optical viewing through the endoscope system.

The cholangiography catheter is typically a Taut catheter characterized by a bulbous tip at the distal end with a fluid outlet which becomes centrally disposed in the cystic duct when properly inserted. The catheter is loaded from its proximal end through one end of a tubular guide and emerges at the other end for connection to a source of dye. The guide is usually straight where the catheter exits, making it very difficult to manipulate the catheter tip through the cystic duct wall with the tip properly directed toward the common duct. The procedure is further complicated by the fact that the duct is usually clamped around the catheter by means of a separately applied clamp. Typically, several instruments are required to accomplish these tasks. Some instruments have been devised for the express purpose of simplifying the procedure. For example, one such instrument includes a built-in clamp disposed adjacent to the catheter a fixed distance short of the distal end thereof. The catheter tip is first introduced through the incision while the clamp remains proximally spaced from the cystic duct. After the catheter tip is correctly positioned, the entire instrument is moved forward until the clamp surrounds the duct, whereupon it is clamped and the dye injected. While some improvement may result, it is still difficult to maneuver the catheter tip into the proper position and direction in the cystic duct.

It is therefore an object of the invention to provide a novel and improved instrument, suitable for surgical procedures such as operative cholangiography associated with a laparoscopic cholecystectomy, in which a catheter can be readily inserted in the cystic duct for injecting a contrast fluid medium without having the medium escape into the abdominal cavity and obscure the biliary ducts while X rays are taken for the presence of gallstones, and without impairing visibility of the surgical site to the surgeons.

Another object is to provide a single surgical instrument which can be readily inserted into a cavity through a narrow tube for guiding the distal end of a catheter through an opening in the wall of a pliable channel with its tip extending along the length of the channel, and which can be clamped around the channel at the distal end of the catheter to prevent any fluid injected into the channel from escaping through the opening into the cavity.

Further objects include the provision of an instrument which is easier to use and to disassemble for sterilization; the reduction of the time required for the surgical procedure; and the provision of an instrument which is self-clamping while X-rays are taken.

Briefly, these objects and other aspects of the invention are accomplished with a catheter guide and clamp combined in a single surgical instrument manipulatable through a conventional trocar. The catheter guide includes an elongate tube with an oblique opening at the tip for laterally deflecting the distal end of a catheter in a channel such as a cystic duct. The clamp is operated from the proximal end of a stem slidable along the length of the catheter guide. As the catheter tip is introduced through an incision in the channel wall, the instrument is rotated from the distal end to turn the oblique opening of the guide in a desired direction along the channel before extending the catheter tip. During insertion of the catheter tip into the incision in the channel wall, the clamp jaws are held in a withdrawn position proximal with respect to the oblique opening of the guide. After the catheter tip is in place, the clamp jaws are moved forward to a position laterally opposite to the opening of the guide, and a plunger, manipulated at the proximal end of the instrument, closes the clamp jaws to seal the channel wall around the catheter in front of the guide opening, thereby preventing any fluid injected into the channel through the catheter from escaping through the incision. The handle is spring-loaded to urge the clamp to a normally closed position while X rays are taken.

For a better understanding of the invention, reference will be made to the following detailed description taken in conjunction with the accompanying drawings.

BRIEF DESCRIPTION OF THE DRAWINGS

FIG. 1 is a longitudinal plan view of a catheter guide and clamp according to the invention, suitable for use in an operative cholangiography associated with a laparoscopic cholecystectomy;

FIG. 2 is a longitudinal side view of the instrument of FIG. 1;

FIG. 3 is an enlarged cross sectional view of the instrument taken on plane 3—3 of FIG. 1;

FIG. 4 is an enlarged longitudinal cross section of a distal end portion of the instrument taken on plane 4—4 of FIG. 1;

FIG. 5 is an enlarged longitudinal cross section of a proximal end portion of the instrument of FIG. 1;

FIGS. 6a and 6b are enlarged representations of a clamp on the distal end of the instrument of FIG. 1 in the closed and open positions, respectively.

DETAILED DESCRIPTION

Figure 7A:
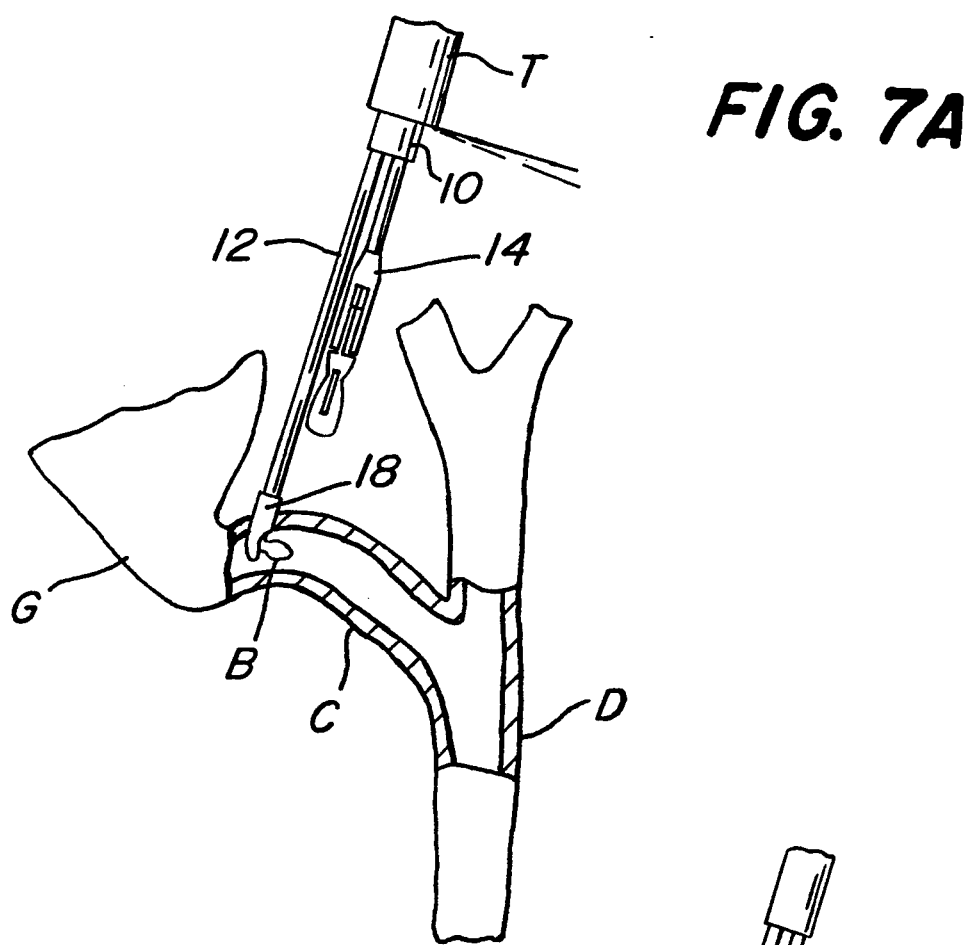
FIGS. 7a and 7b are anterior views of a portion of the biliary ducts with the instrument in unclamped and clamped positions, respectively.

Referring now to the drawings, wherein like reference characters designate like or corresponding parts throughout the several views, there is shown in FIG. 1 and 2 an instrument 10 according to the invention for use in surgical procedures such as operative cholangiography. Instrument 10 includes a catheter guide 12 and clamp 14 disposed lengthwise in a straight sleeve 16 suitably configured for insertion through a conventional trocar having an inside diameter of 5 mm. and a length of 35 cm.

As best seen in FIG. 3, catheter guide 12 is a hollow tube having a straight section 12a fixed along its length to the interior of sleeve 16. As shown in FIG. 2 a distal section 12b extends beyond the one end 16a of sleeve 16. The guide terminates in a hollow tip 18. Referring to FIGS. 1 and 2, proximal section 12c of guide 12 extends beyond the other end 16b of the sleeve and terminates in a finger grip 20. The enlarged view in FIG. 4 shows the distal extremity of tip 18 as including a curved wall 18a for obliquely deflecting a catheter out through an aperture 18b in the opposite side.

Referring now to FIG. 2, clamp 14 comprises a tubular clamp guide 22 fixed along its length to the interior of sleeve 16. The clamp guide extends proximally beyond end 16b of tube 16, and terminates in a finger grip 24. A clamp actuator tube 26 (FIG. 3), slidable lengthwise in clamp guide 22, is bifurcated at its distal end 26a (FIG. 2) for pivotally supporting a pair of scissors-like jaws 32 at pin 34 (FIGS. 6A and 6B) in close proximity to aperture 18b of the catheter guide. Jaws 32 are articulated between open and closed positions by a clamp actuator stem 36 slidable lengthwise in actuator tube 26 and are pivotally connected at the distal end through oppositely disposed spreader links 38. Jaws 32 are positioned with their pivotal axis normal to the length of catheter guide 12 and translatable in a plane radially extending therefrom. This ensures that jaws 32 will clamp around the cystic duct in close proximity to aperture 18b. The proximal end of stem 36 extends into a cylindrical chamber 40 of housing 28 and is operated on by a plunger 42 (FIG. 5) attached thereto. A compression spring 44 within chamber 40 urges plunger 42 against an end cap 46, thereby urging jaws 32 to the normally closed position shown in FIG. 6A. Finger grips 48 extending from opposite sides of housing 28 and thumb actuator 50 slidably extending through end cap 46 enable plunger 42 and stem 36 to be manipulated by one hand to compress spring 44 and thereby move jaws 32 to the open position of FIG. 6B.

Figure 7B:
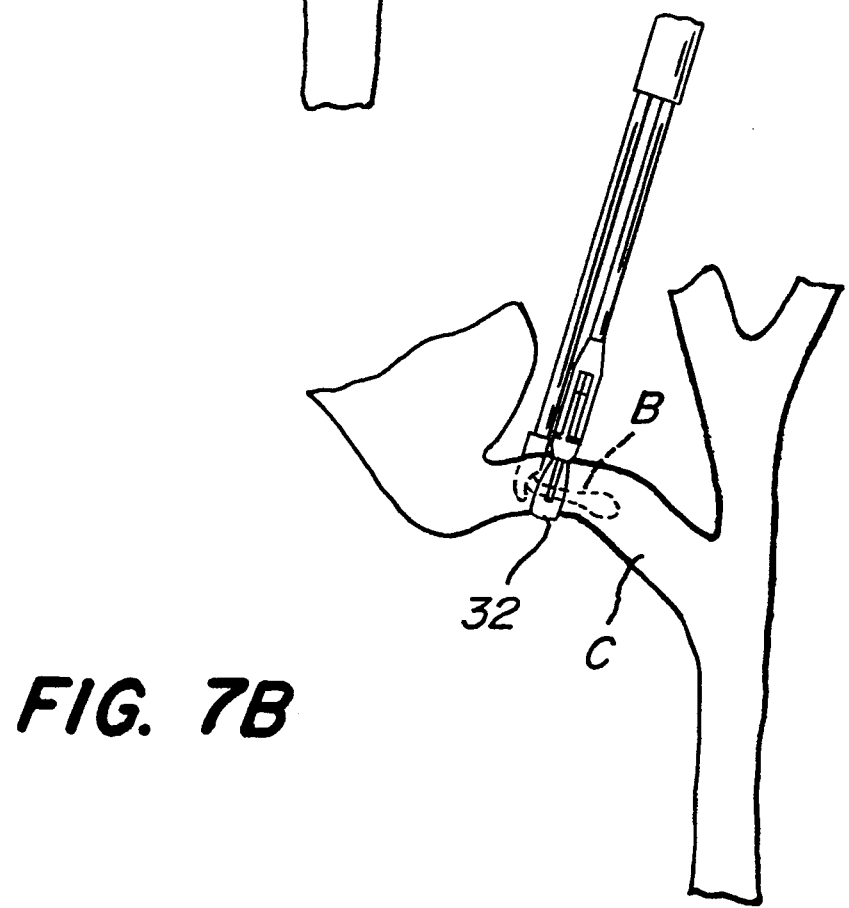

Use of the present invention will be described with reference to FIGS. 7A and 7B which schematically represents two stages in the performance of an operative cholangiography associated with a laparoscopic cholecystectomy. After an incision is made in the cystic duct C near the gallbladder G, the cutting instrument (not shown) is withdrawn from trocar T and replaced by instrument 10 having a catheter functionally positioned in guide 12. With clamp 14 drawn out of the way, trocar T and catheter guide 12 are manipulated to introduce catheter tip B into the incision with its aperture 18b directed toward the common duct D. At this time, the clamping jaws are withdrawn to a position proximal in relation to the position of tip 18. The curvature of the opposite wall 18a of tip 18 obliquely deflects the catheter into the cystic duct C which, in the illustrated example, utilizes a Taut catheter. The catheter may then be extended further into the duct while continuing to deflect toward the common duct D as it moves. When a sufficient length of catheter has been extended for clamping, finger grip 48 and thumb actuator 50 are manipulated to open jaws 32 against the force of spring 44 while actuator tube 26 is slid along the length of sleeve 16 relative to guide 12 until jaws 32 are on opposite sides of cystic duct C. Thumb actuator 50 is released, allowing jaws 32 to close tightly clamping duct C around the catheter. Radiopaque dye may then be injected into the biliary duct with assurance that none will leak through the incision into the abdominal cavity and obscure visibility.

Some of the many advantages of the invention should now be readily apparent. For instance, a novel and improved instrument is provided for use in operative cholangiography associated with a laparoscopic cholecystectomy. The instrument enables a catheter to be manipulated through a trocar into the cystic duct in the direction toward the common duct. It provides a single instrument for conveniently clamping the duct around the catheter to prevent any contrast medium injected through the catheter from escaping through the incision. The instrument is operated with considerable ease and reduction in time, is self-clamping and is particularly suitable for disassembly and sterilization. The fact that the jaws are withdrawable prevents the jaws from interfering with the introduction of the catheter into the cystic duct.

Various changes in the details, steps, and arrangement of parts, which have been herein described and illustrated in order to explain the nature of the invention, may be made by those skilled in the art within the principle and scope of the invention as expressed in the appended claims.

We claim:

1. An instrument suitable for use in operative cholangiography associated with a laparoscopic cholecystectomy wherein a trocar is inserted through an incision, and a catheter is used to introduce a fluid contrast medium into the cystic duct, comprising in combination:

a catheter;
  guide means for extending through said trocar for guiding a distal section of said catheter through an incision into the cystic duct, said guide means including diverting means for changing the direction of movement of the catheter so that it approaches the cystic duct in a first direction transverse to the length of the cystic duct, and is then diverted for movement along a first path within said cystic duct, said first path extending in a direction along the length of the cystic duct;
  clamp means for clamping the cystic duct against the catheter; and
  means for supporting said clamp means in said trocar for longitudinally sliding movement relative to said guide means along a second path which intersects said first path;
  said clamp means having oppositely disposed jaws movable between an open position and a closed position, said jaws having clamping surfaces engageable with the cystic duct when the catheter extends along the length of the cystic duct, said clamping surfaces being disposed sufficiently close to each other, when the jaws are in said closed position, that the cystic duct is compressed against the catheter sufficiently tightly to prevent fluid contrast medium from flowing through the duct about the catheter;
whereby fluid contrast medium injected by said catheter extending through said guide means into the cystic duct is prevented, by said clamp means, from escaping through the incision.

2. An instrument according to claim 1 wherein said guide means comprises a substantially straight guide tube for slidably receiving said catheter, said tube having proximal and distal ends and having an aperture formed in the side of said tube adjacent to the distal end thereof, and wherein said diverting means is arranged to cause the catheter to project through said aperture in a direction which is oblique with respect to the length of said substantially straight guide tube.

3. An instrument according to claim 2 wherein said clamp means includes an actuator tube movable lengthwise relative to said guide tube, an actuator stem movable lengthwise within said actuator tube, and in which said jaws are operatively connected to the distal ends of said actuator tube and stem; whereby said jaws are movable between a retracted position remote from said aperture and a clamping position adjacent to said aperture.

4. An instrument according to claim 3 wherein said clamp means includes bias means for urging said jaws to said closed position.

5. An instrument according to claim 4 wherein said bias means include a housing connected to the proximal end of said actuator tube, a plunger connected to the proximal end of said actuator stem and slidable in said housing, and force exerting means, within said housing, operatively connected between said plunger and said housing.

6. An instrument according to claim 3 wherein said jaws are pivotally articulated on an axis normal to the length of said guide tube and translatable in a plane along the length of said guide tube.

7. A surgical instrument for introducing a catheter through an opening in the pliable wall of an anatomical duct, with the tip of the catheter extending along the length of the duct, comprising, in combination:
a catheter;
  tubular means for guiding the tip of the catheter into the anatomical duct, through the duct opening, said tubular guiding means including diverting means for changing the direction of movement of the catheter so that it approaches the duct in a first direction transverse to the length of the duct, and is then diverted for movement along a first path within said duct, said first path extending along the length of the duct;
  clamp means for clamping the pliable wall of the duct around the tip of the catheter; and
  means for supporting said clamping means for longitudinal sliding movement relative to said tubular means along a second path which intersects said first path;
  said clamp means having oppositely disposed jaws movable between an open position and a closed position, said jaws having clamping surfaces engageable with the duct when the catheter extends along the length of the duct, said clamping surfaces being disposed sufficiently close to each other, when the jaws are in said closed position, that the duct is compressed against the catheter sufficiently tightly to prevent fluid from flowing through the duct about the catheter.
whereby fluid injected into the duct through the catheter is prevented, by said clamping means, from escaping through the opening.

8. An instrument according to claim 7 wherein said tubular guiding means is substantially straight and has proximal and distal ends, wherein said tubular guiding means includes an aperture formed in the side of said tube adjacent to the distal end thereof, and wherein said diverting means is arranged to cause the catheter to project through said aperture in a direction which is oblique with respect to the length of said tube.

9. An instrument according to claim 8 wherein said clamp means includes two actuator members movable lengthwise relative to said straight section and adjacent to said straight section, and said jaws are operatively connected respectively to the distal ends of said actuator members; whereby said jaws are movable from a retracted position remote from said duct to a position adjacent to said duct for clamping the pliable wall of the duct about the exposed tip of a catheter.

10. An instrument according to claim 9 wherein said clamp means includes force-exerting means for urging said jaws to said closed position.

11. An instrument according to claim 10 wherein:
  said force-exerting means includes a housing connected to the proximal end of one of said actuator members, a plunger connected to the proximal end of the other of said actuator members and slidable in said housing, and a spring within said housing operatively connected between said plunger and said housing.

12. An instrument according to claim 9 wherein said jaws are pivotally articulated on an axis normal to the length of said straight section and translatable in a plane along the length of said straight section.

13. A surgical instrument for use in laparoscopic cholecystectomy comprising:
  means, comprising a flexible catheter, for injecting radiopaque fluid into the cystic duct of a patient;
  an elongated tubular catheter guide having an internal passage, with proximal and distal ends, for receiving said flexible catheter, said internal passage extending along the length of the guide and said internal passage being smoothly curved at said distal end whereby the catheter projects from the passage along a first path transverse to the length of the guide;

an elongated clamp structure having proximal and distal ends and extending lengthwise alongside said catheter guide, said clamp structure being secured in parallel relationship to said catheter guide, but being movable relative to said catheter guide in the longitudinal direction, said clamp structure comprising a pair of oppositely disposed clamping jaws at said distal end and manipulable means, located at said proximal end, for moving said jaws between an open position and a closed position;

wherein said jaws have clamping surfaces engageable with the cystic duct when the catheter extends along the length of the cystic duct, said clamping surfaces being disposed sufficiently close to each other, when the jaws are in said closed position, that the cystic duct is compressed against the catheter sufficiently tightly to prevent radiopaque fluid from flowing through the cystic duct about the catheter;

wherein the clamp structure is positioned on the side of said catheter guide toward which the catheter projects from said passage; and wherein the clamp structure is movable, along a second path which intersects said first path, in the proximal direction to an extent such that the jaws are positioned proximally relative to the distal end of the catheter guide, and in the distal direction to an extent such that the jaws are positioned laterally opposite to said curved distal end of the internal passage whereby the jaws are capable of clamping the cystic duct around the catheter projecting transverse to the length of the catheter guide from said curved distal end of said internal passage.

* * * * *